United States Patent
Mawhirt et al.

(10) Patent No.: US 7,379,167 B2
(45) Date of Patent: May 27, 2008

(54) HEMOGLOBIN TEST STRIP AND ANALYSIS SYSTEM

(75) Inventors: James A. Mawhirt, Brooklyn, NY (US); Ted Lee, Matawan, NJ (US); Supinan R. Naphuket, Edison, NJ (US); Charles E. Toms, Colonia, NJ (US); Wai Law, Moorestown, NJ (US); Catherine Cimini, Somerset, NJ (US)

(73) Assignee: International Technidyne Corporation, Edison, NJ (US)

( * ) Notice: Subject to any disclaimer, the term of this patent is extended or adjusted under 35 U.S.C. 154(b) by 194 days.

(21) Appl. No.: 10/364,256

(22) Filed: Feb. 11, 2003

(65) Prior Publication Data

US 2004/0156037 A1 Aug. 12, 2004

(51) Int. Cl.
*G01N 33/48* (2006.01)
*G01N 21/00* (2006.01)
*G01N 21/77* (2006.01)
*C12Q 1/00* (2006.01)

(52) U.S. Cl. .......................... 356/39; 356/40; 422/58; 435/4; 436/169

(58) Field of Classification Search .................. 356/39, 356/40, 244, 246
See application file for complete search history.

(56) References Cited

U.S. PATENT DOCUMENTS

| | | | |
|---|---|---|---|
| 4,057,394 A | 11/1977 | Genshaw | 23/230 |
| 4,935,346 A | 6/1990 | Phillips et al. | 435/14 |
| 5,064,282 A * | 11/1991 | Curtis | 356/40 |
| 5,304,468 A * | 4/1994 | Phillips et al. | 435/14 |
| 5,526,120 A | 6/1996 | Jina et al. | 356/446 |
| 5,605,837 A * | 2/1997 | Karimi et al. | 436/14 |
| 5,755,231 A * | 5/1998 | Krantz et al. | 600/368 |
| 6,055,060 A | 4/2000 | Bolduan et al. | 356/433 |
| 6,284,550 B1 * | 9/2001 | Carroll et al. | 436/514 |
| 6,312,888 B1 * | 11/2001 | Wong et al. | 435/4 |
| 6,315,951 B1 | 11/2001 | Markart | 422/61 |
| 6,541,266 B2 * | 4/2003 | Modzelewski et al. | 436/95 |
| 6,670,192 B1 * | 12/2003 | Galen et al. | 422/67 |
| 6,766,817 B2 | 7/2004 | da Silva | 137/1 |

OTHER PUBLICATIONS email from Elson Silva to Paul Schwartz dated May 3, 2006, pp. 1-3 relating to U.S. Patent 6,766,817.

* cited by examiner

*Primary Examiner*—Gregory J. Toatley, Jr.
*Assistant Examiner*—Roy M. Punnoose
(74) *Attorney, Agent, or Firm*—Duane Morris LLP

(57) ABSTRACT

The apparatus and method for quickly measuring the hemoglobin content of a sample of blood uses a light reflectance measurement of the hemoglobin sample lysed in a membrane. The reflection is inversely proportional to hemoglobin concentration. A blood sample is loaded on to a nylon mesh and dispersed within a nylon membrane, both of which have been treated with a hemolyzing agent and surfactant, and air-dried. As soon as the blood sample contacts the reagent on the membrane, the red blood cells are lysed and the hemoglobin molecules are released and dispersed into the membrane by the action of surfactant. The hemoglobin apparatus emits light at 522 nm to the reflective surface of the membrane. The intensity of the reflected light is measured by a detector in less than 29 seconds. The intensity of the reflected light is converted to hemoglobin concentration, g/dL, or mmol/L by an interpolative comparison with stored reflection data indicative of known hemoglobin contents.

26 Claims, 8 Drawing Sheets

Precision Study

| | % Remission | | | | % Hemoglobin | | | |
|---|---|---|---|---|---|---|---|---|
| | 4 % Hb | | 8 % Hb | | 4 % Hb | | 8 % Hb | |
| | BAC[1] | AOT[2] | BAC | AOT | BAC[1] | AOT[2] | BAC | AOT |
| | 67.5 | 67.8 | 44.2 | 42.8 | 4.4 | 4.6 | 8.6 | 9.2 |
| | 66.6 | 68.2 | 44.8 | 41.5 | 4.5 | 4.6 | 8.5 | 9.6 |
| | 68.2 | 66.6 | 44.7 | 43.3 | 4.3 | 4.8 | 8.5 | 9.1 |
| | 68.8 | 68.8 | 43.9 | 43.7 | 4.3 | 4.5 | 8.7 | 9.0 |
| | 66.2 | 67.6 | 43.5 | 42.6 | 4.6 | 4.7 | 8.8 | 9.3 |
| | 67.2 | 69.1 | 43.6 | 42.5 | 4.5 | 4.5 | 8.8 | 9.3 |
| | 66.6 | 67.9 | 43.3 | 42.1 | 4.5 | 4.6 | 8.8 | 9.4 |
| | 67.5 | 66.0 | 43.6 | 41.2 | 4.4 | 4.9 | 8.8 | 9.6 |
| | 67.9 | 66.1 | 43.8 | 41.7 | 4.4 | 4.8 | 8.7 | 9.5 |
| | 67.0 | 66.1 | 44.4 | 42.2 | 4.5 | 4.8 | 8.6 | 9.4 |
| | 67.6 | 67.4 | 43.9 | 41.9 | 4.4 | 4.7 | 8.7 | 9.4 |
| | 68.1 | 66.8 | 43.9 | 41.9 | 4.3 | 4.8 | 8.7 | 9.4 |
| | 65.6 | 66.0 | 43.3 | 41.1 | 4.7 | 4.9 | 8.8 | 9.7 |
| | 66.4 | 67.2 | 45.7 | 42.1 | 4.6 | 4.7 | 8.3 | 9.4 |
| | 66.6 | 68.2 | 43.7 | 41.1 | 4.5 | 4.6 | 8.7 | 9.7 |
| Average | 67.2 | 67.3 | 44.0 | 42.1 | 4.5 | 4.7 | 8.7 | 9.4 |
| Std. Dev. | 0.9 | 1.0 | 0.7 | 0.8 | 0.1 | 0.1 | 0.2 | 0.2 |
| % CV | 1.3 | 1.5 | 1.5 | 1.6 | 2.5 | 2.8 | 1.8 | 2.1 |

[1] "BAC" is composed of 2.5 % Benzalkonium Chloride, 2.5% Saponin, and a small amount of HCl.

[2] "AOT" is composed of 1.5% Aerosol OT, 2.5% Saponin, 2.5% Maltodextrin, and a small amount of Phenol and Tartrazine

Fig. 4

Hemoglobin Measurement with 4 different Systems

| Hemoglobin % | | | | | |
|---|---|---|---|---|---|
| ITC* | 4.3 | 8.2 | 12.2 | 16.1 | 20.1 |
| Coulter | 4.3 | 8.2 | 12.2 | 16.1 | 20.2 |
| Hemocue | 4.4 | 8.5 | 12.5 | 16.6 | 20.8 |
| Drabkin** | 4.4 | 8.3 | 12.1 | 15.6 | 20.6 |

*With 2.5% saponin and 2.5% benzalkonium chloride
**Reference cyanmethemoglobin method at 540 nm.

Fig. 5

Hb Detection Method: *UMM Hb-Meter (High Intensity)*
37 sec reading by LED 1
12.5 ul 2.5% Saponin + 2.5% BzkCl

| Trial # | 4.2 | 8.3 | 12.2 | 13.5 | 17.1 | 19.7 |
|---|---|---|---|---|---|---|
| 1 | 67 | 44.6 | 30.9 | 28.4 | 21.2 | 17.3 |
| 2 | 65.4 | 45.8 | 30.9 | 28.2 | 20.7 | 17 |
| 3 | 66.9 | 44.4 | 30.3 | 27.1 | 21.8 | 17.4 |
| 4 | 66 | 44.8 | 29.3 | 27.7 | 21.7 | 16.4 |
| 5 | 66.7 | 44.3 | 30.2 | 27 | 20.9 | 16.9 |
| average | 66.4 | 44.8 | 30.3 | 27.7 | 21.3 | 17.0 |
| sidev | 0.7 | 0.6 | 0.7 | 0.6 | 0.5 | 0.4 |
| % CV | 1.0 | 1.3 | 2.2 | 2.3 | 2.3 | 2.3 |
| ratio: R/Hb | -5.3 | -3.7 | -2.0 | -1.8 | -1.6 | |

Wbsample#MJ120400(10ul); strip wide-normal #120100(12.5ul 40C 5%RH 30 min.); rgt#120100; UMM# 19(#102)

Calculation: X=EXP[(Y-112.6)/-32.341]

| Trial # | 4.2 | 8.3 | 12.2 | 13.5 | 17.1 | 19.7 |
|---|---|---|---|---|---|---|
| 1 | 4.0958528 | 8.1873823 | 12.505957 | 13.51103 | 16.880076 | 19.043465 |
| 2 | 4.3035823 | 7.8891597 | 12.505957 | 13.594842 | 17.143074 | 19.220936 |
| 3 | 4.108537 | 8.2381708 | 12.740137 | 14.065191 | 16.569799 | 18.984672 |
| 4 | 4.224477 | 8.136907 | 13.140222 | 13.806655 | 16.621113 | 19.580857 |
| 5 | 4.1340233 | 8.2636831 | 12.779591 | 14.108749 | 17.037387 | 19.280461 |
| average | 4.2 | 8.1 | 12.7 | 13.8 | 16.9 | 19.2 |
| sidev | 0.1 | 0.2 | 0.3 | 0.3 | 0.3 | 0.2 |
| % CV | 2.1 | 1.8 | 2.0 | 1.9 | 1.5 | 1.2 |

1.5% Sodium diocryl sulfosuccinate (AOT)
2.5% M-700
2.5% Saponin
20 $^{Hb}/_{ml}$ Tartrazine
0.005% Phenol
$\lambda$ = 522 (HI)

| Trial | % Hb | | | | | |
|---|---|---|---|---|---|---|
| | 4.2 | 8.3 | 13.1 | 15.3 | 17.5 | 20.3 |
| 1 | 72.6 | 45.4 | 30.3 | 23.5 | 19.6 | 15.6 |
| 2 | 73.4 | 46.3 | 29.7 | 23.4 | 19.8 | 16.2 |
| 3 | 70.4 | 43.2 | 28.7 | 23.6 | 19.5 | 15.9 |
| 4 | 73.8 | 44.7 | 29.3 | 22.9 | 20.0 | 16.5 |
| 5 | 73.3 | 44.1 | 29.2 | 22.8 | 19.9 | 16.4 |
| mean | 72.70 | 44.74 | 29.44 | 23.24 | 19.76 | 16.12 |
| $S^{n-1}$ | 1.356 | 1.189 | 0.598 | 0.365 | 0.207 | 0.370 |
| % C | 1.9 | 2.7 | 2.0 | 1.6 | 1.0 | 2.3 |
| $^a/_{a(Hb)}$ | ✕ | -6.8 | -3.2 | -2.8 | -1.6 | -1.3 |
| Deriv. | -8.6 | -4.4 | -2.8 | -2.4 | -2.1 | -1.8 |

M-700-Dioctyl sulfosuccinate, Na$^+$ salt=Saponin Reagent $y = -36.275\ln(x) + 123.36$
$R^2 = 0.9951$ % Hb $[Hb] = e^{((R-123.36)/-36.275)}$

| Trial | % Hb | | | | | |
|---|---|---|---|---|---|---|
| | 4.3 | 8.4 | 12.6 | 15.4 | 17.6 | 20.5 |
| 1 | 4.05 | 8.58 | 13.01 | 15.69 | 17.47 | 19.50 |
| 2 | 3.96 | 8.37 | 13.22 | 15.73 | 17.37 | 19.18 |
| 3 | 4.31 | 9.11 | 13.59 | 15.64 | 17.52 | 19.34 |
| 4 | 3.92 | 8.74 | 13.37 | 15.95 | 17.28 | 19.03 |
| 5 | 3.97 | 8.89 | 13.41 | 15.99 | 17.32 | 19.08 |
| mean | 4.04 | 8.74 | 13.32 | 15.80 | 17.39 | 19.23 |
| $s_{n-1}$ | 0.2 | 0.3 | 0.2 | 0.2 | 0.1 | 0.2 |
| % C | 3.8 | 3.3 | 1.6 | 1.0 | 0.6 | 1.0 |

Clinical Studies: Patient Samples (15ul)

Rgt# 121100; 2.5% saponin+25%BzkCl; pH 2.3
Strip #RS121900(5-mm hole); 60C 5%RH 7.5 min; 13 UL
Calculation: X=EXP[(Y-112.27)/-32.595] from std. curve data %Hb determined by Coulter MDB CLL w/o remission/Female; 12.5%

|  | UMM#102 | | Hemocue |
|---|---|---|---|
|  | % R | Hb (g/dL) | Hb (g/dL) |
| 1 | 31.3 | 12.0 | 12.7 |
| 2 | 31.1 | 12.1 | 12.6 |
| 3 | 30.9 | 12.1 | 12.7 |
| 4 | 30.6 | 12.3 | 12.7 |
| average stdev %CV | 31.0 0.3 1.0 | 12.1 0.1 0.9 | 12.7 0.0 0.4 |

Lymphomia/Male Hypochemia; 7.6%

|  | UMM#102 | | Hemocue |
|---|---|---|---|
|  | % R | Hb (g/dL) | Hb (g/dL) |
| 1 | 47.0 | 7.4 | 7.6 |
| 2 | 47.1 | 7.4 | 7.6 |
| 3 | 47.7 | 7.2 | 7.7 |
| 4 | 46.9 | 7.4 | 7.7 |
| average stdev %CV | 47.2 0.4 0.8 | 7.4 0.1 1.1 | 7.7 0.1 0.8 |

Polycythemi/Male; 17.35%

|  | UMM#102 | | Hemocue |
|---|---|---|---|
|  | % R | Hb (g/dL) | Hb (g/dL) |
| 1 | 20.6 | 16.6 | 17.7 |
| 2 | 21.1 | 16.4 | 17.8 |
| 3 | 21.1 | 16.4 | 17.3 |
| 4 | 21.0 | 16.4 | 17.7 |
| average stdev %CV | 21.0 0.2 1.1 | 16.5 0.1 0.7 | 17.6 0.2 1.3 |

Hypochimia/Female; 6.6%

|  | UMM#102 | | Hemocue |
|---|---|---|---|
|  | % R | Hb (g/dL) | Hb (g/dL) |
| 1 | 52.4 | 6.3 | 6.6 |
| 2 | 52.3 | 6.3 | 6.6 |
| 3 | 52.6 | 6.2 | 6.5 |
| 4 | 51.9 | 6.4 | 6.7 |
| average stdev %CV | 52.3 0.3 0.6 | 6.3 0.1 0.9 | 6.6 0.1 1.2 |

Hypochimia/Male; 9.25%

|  | UMM#102 | | Hemocue |
|---|---|---|---|
|  | % R | Hb (g/dL) | Hb (g/dL) |
| 1 | 39.6 | 9.3 | 9.4 |
| 2 | 39.1 | 9.4 | 9.3 |
| 3 | 38.8 | 9.5 | 9.5 |
| 4 | 38.3 | 9.7 | 9.6 |
| average stdev %CV | 39.0 0.5 1.4 | 9.5 0.2 1.7 | 9.4 0.1 1.0 |

Fig. 8

Chronic lymphocytic leukemia (CLL)
    malignancy of WBC (lymphocytes); causing an increase of these cells in blood & bone marrow
Hypochromia
    anemic condition in/wc the %Hb in RBC is less than normal range

HEMOGLOBIN TEST STRIP AND ANALYSIS SYSTEM

FIELD OF THE INVENTION

This invention relates to a hemoglobin test and, more particularly, to a disposable, inexpensive test strip and meter for rapid determination of the total hemoglobin content of a whole blood sample.

BACKGROUND OF THE INVENTION

As one can understand, the prior art is concerned with making medical tests available to the consumer at reasonable prices so that patients, nurses, as well as inexperienced individuals can monitor medical conditions. In particular, a widely used and familiar test concerns the measurement of glucose. The glucose test system is designed to be used by an individual, for example, a person who has diabetes, and is available over-the-counter. As one can ascertain, the glucose test market is enormous. Significant work has been done over many years by many large companies to improve the glucose test procedure and to reduce its cost and streamline the manufacturing techniques and test systems used.

In the glucose test system, a test strip is employed. The patient places a drop of blood on the test strip, the drop of blood having being obtained by conventional incision making or fingerstick devices, as are well known. The system then utilizes the test strip and essentially measures the glucose, by means of a glucose test and displays the results on a conventional meter.

The present apparatus employs optical detection to determine the hemoglobin content of a whole blood sample and uses a reagent that is free of cyanides, azides and carcinogens to enable the instrumented assessment of the hemoglobin content of whole blood. The reagent formulation is impregnated into a suitable mesh/membrane matrix that serves as an optical baseline for the optical measurement. The test method utilizes a common diffuse reflectance optical technique, operating on the test or reflecting surface of the membrane. The membrane surface is saturated with the red-colored hemoglobin and the system accurately measures the hemoglobin content of the whole blood sample and displays the results on a meter. A single drop of blood is applied to the test area of the test strip. The test well area is covered by the hydrophilic mesh. This mesh covering facilitates dispersion of the blood across the entire membrane upper surface. The uniform dispersion of the sample initially results in uniform infiltration of the membrane matrix. Uniform dispersion and infiltration results in uniform coloration of the membrane test surface. The lower surface receives the released hemoglobin and is discolored. The test sample blood is obtained from a fingerstick or other device. The test actually requires less than one drop of blood and is not compromised by additional sample volume. Excess sample is captured and restrained by the mesh and the membrane matrix. The membrane pores are blocked by non-hemolysed red cells and hemolysed cell debris. The mesh and membrane infiltration volume is therefore limited and the test surface, as a result, is not wetted but rather just colored. Wetting creates undesirable specular reflectance.

Additional sample volume is easily dealt with by the mesh membrane matrix. The test results are not compromised by the excess sample volume. Low volume, however, can cause errors in the system. The system, therefore, has a low volume test within the software. The hemoglobin content is rapidly determined and displayed after only 5 to 29 seconds.

The meter performance has been specifically and favorably compared to existing methods, including devices supplied by other companies. The test can be performed at the point of care, in a physician's office lab, in a hospital or any other environment where a patient is at risk and whose hemoglobin content must be known to facilitate medical diagnosis and treatment. The meter is portable and battery-powered, utilizing a common readily available coin type battery. As will be explained, the test strips employed are durable with a good shelf life. The twenty five test strip container has a built-in dessicator to help preserve the unused test strips in the container during use. Each container will be labeled and marked with a lot number, date of manufacture and a characteristic lot-specific code number. As will be explained, the system is user friendly and requires only a small drop of blood for test purposes. The sample target spot is highlighted by test strip graphics and the surrounding area of the meter is flat allowing easy access, reducing the potential for spillage or contamination. The test strip entry surround, including the sample introduction area, is easily removed for cleaning or replacement as required. The entry surround is configured as a simple, on/off piece for cleaning or a potentially disposable part. The entire instrument is also able to be easily cleaned and disinfected.

It is also an object to provide a simple and reliable test strip and meter for measuring the hemoglobin content of a blood sample.

SUMMARY OF THE INVENTION

An apparatus to determine the hemoglobin content of a whole blood sample is described. The apparatus uses a highly productionized test strip configuration. The test strips consist of a base, made of a plastic film, a dispersion mesh pad and a membrane pad bonded to the base. The dispersion mesh and the membrane matrix are impregnated with a reagent compound and dried. The dispersion mesh and the membrane matrix contain the dried reagent which, when contacted by liquid blood reacts with the blood red cells and releases the hemoglobin from the red cells. The hemoglobin disperses across and through the mesh initially, filling the capillary hole. The blood then saturates and infiltrates the membrane to such a degree that the membrane test surface is discolored red. Excess sample volume is restricted from the membrane, so the membrane operates to utilize a constant sample of blood. The membrane colors but does not wet. The purpose is for the simple, easy and quick determination of a person's hemoglobin level in a "point of care" format. The matrix membrane surface is sampled by a suitable light source where the reflectance of light at a specific frequency is inversely proportional to the degree of color of the membrane surface and therefore to the hemoglobin content.

BRIEF DESCRIPTION OF THE DRAWINGS

FIG. 4 shows Table 1 which is a precision study between different reagents which can be used to impregnate a membrane according to this invention.

FIG. 5 depicts Table 2 showing hemoglobin measurements utilizing four different systems depicting the degree of correlation of five levels of Hemoglobin tests according to this invention.

FIG. 6A are data derived from this invention and 6C are data from a prior art spectrometer device.

FIG. 8 shows a series of tables including abnormal patient studies with different hemoglobin contents and depicting the values of the hemoglobin contents for the abnormal blood of various different individuals compared to a standard method (hemocue).

Appendix A is a program which can be incorporated in an EEPROM for measuring the hemoglobin content of the blood sample according to this invention.

DETAILED DESCRIPTION OF THE DRAWINGS

Figure 1:
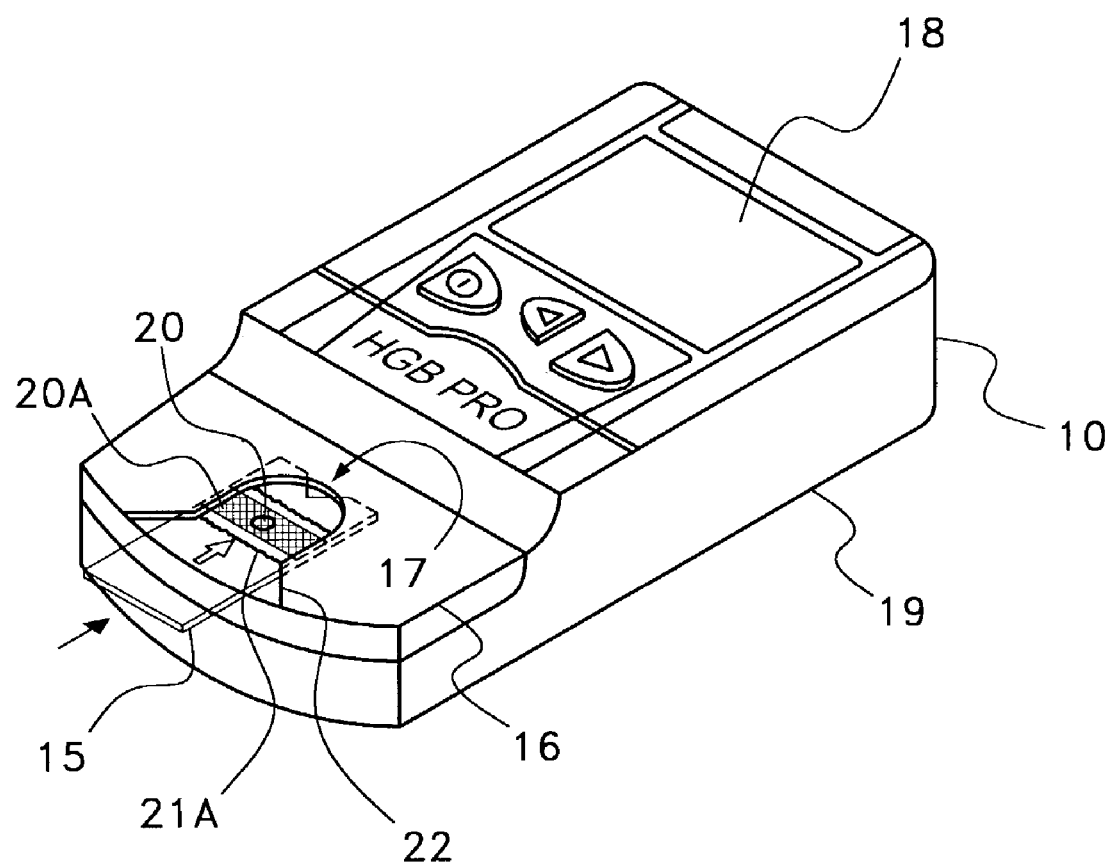
FIG. 1 is a perspective view of a hemoglobin meter according to this invention showing the meter accommodating a test strip according to this invention.

Referring to FIG. 1, there is shown an instrument 10 for measuring the hemoglobin content of a whole blood sample. Essentially, as seen, the unit is referred to as a Hgb Meter designated the "Hgb Meter". The term "Hgb" is the designation for hemoglobin. As one understands, hemoglobin is the red pigment of blood whose major function is to transport oxygen from the lungs to the tissues. It is a protein of four polypeptide chains, each bearing a heme prosthetic growth which serves as an oxygen binding site. A heme is an iron atom complexed to a porphytin ring, which in combination with the protein globin, forms hemoglobin, which gives it oxygen carrying capacity.

As one can see from FIG. 1, the hemoglobin meter or device includes a housing 19. The housing 19 has a front slot or opening 22 which receives a removable test strip 15. The test strip 15, as will be explained, has a mesh covering 21A, an aperture or test well 20, which connects with the lower test membrane, 21B, not shown. The user inserts a drop of blood into the aperture 20 through the mesh, utilizing the graphic 20A visible through the mesh to accentuate the target aperture. The blood is hemolized and saturated through and into the underlying membrane. The test strip 15 shown also in FIGS. 2A and 2B has a centering notch 17, which assures that when the strip is placed into the slot 22 of the housing 19 and engages a similar feature in the housing, it is always fixed and aligned in a proper and fixed position for performing the test. The front surface of the housing defined by area 16, the Test Strip Holder, is easily cleaned as it is smooth and flat. The Test Strip Holder, 16 is removable for cleaning or as a disposable for replacement. In this manner, if the front end is contaminated it can be discarded. As can be seen, the unit includes a LCD display screen 18 which will display the hemoglobin content of the blood sample. This sample impregnates the matrix associated with the test strip 15, as will be further explained. The display 18 can be a conventional LCD display or any other type of display which is normally utilized in conjunction with hand-held units, such as LEDs or LCDs or others.

The operation of the system is as follows: The strip 15 before receiving the blood is inserted into the front slot 22 associated with housing 16. The user will obtain a drop of blood from a patient or an individual and insert the drop of blood onto the mesh at the targeted aperture 20. The mesh promotes full aperture coverage, whatever volume of blood sample is applied and wherever around the aperture perimeter. The mesh promotes and facilitates full and uniform filling of the aperture capillary area in preparation for uniform infiltration into the membrane, see FIGS. 3A through 3D. The blood will impregnate the membrane uniformly and without wetting. The centering notch 17 assures that the strip is properly located and enables a light emitting diode or LED device, as will be explained, to illuminate and to reflect light off the colored membrane bottom surface to provide an indication of the hemoglobin level of the blood sample placed on the mesh, 21A and aperture, 20 of the test strip, 15. Initially a base line reading is taken to determine the membrane surface reflectance without the blood sample hemoglobin coloration. The user will obtain a drop of blood from a patient or an individual and load the drop of blood into the target aperture 20. See FIG. 3A. The blood will impregnate the mesh, FIG. 3B into the capillary aperture, FIG. 3C and finally infiltrating the membrane, FIG. 3D.

Figures 2, 2A, 2B:
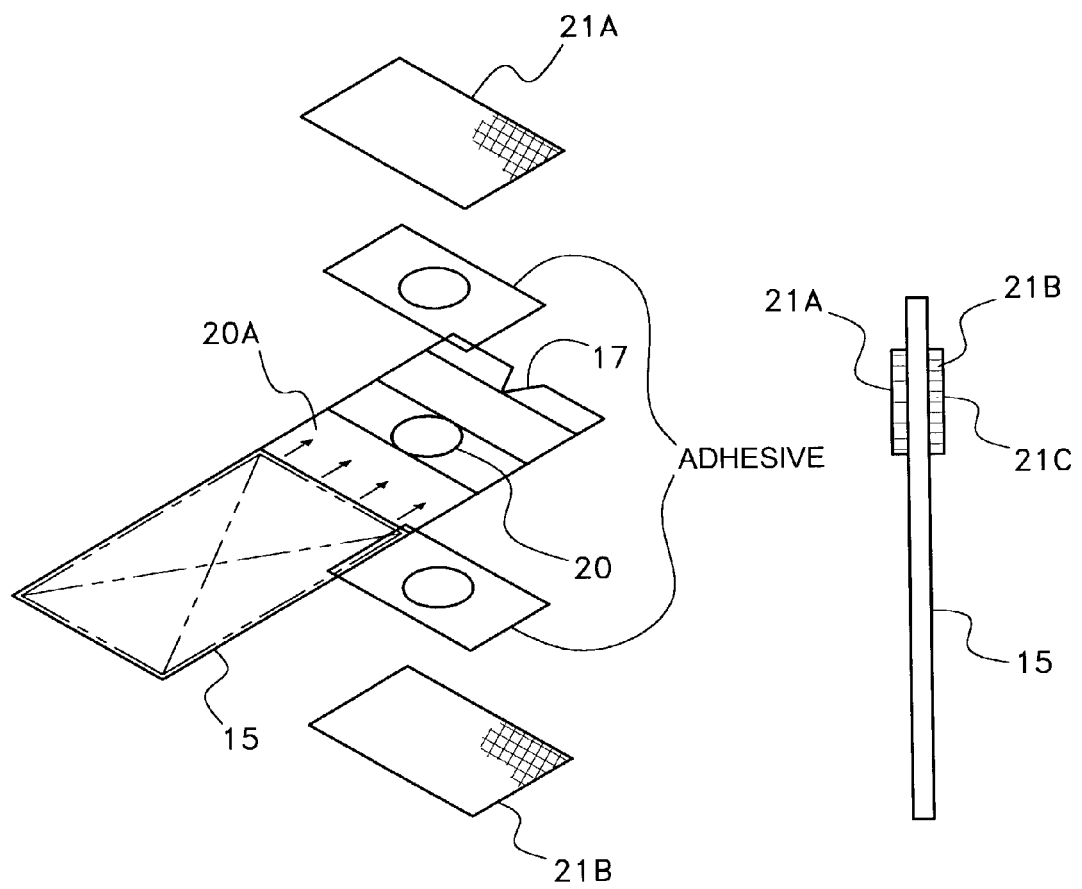
FIG. 2 consists of FIG. 2A and FIG. 2B.
FIG. 2A shows a perspective view of test strip to be utilized with the meter shown in FIG. 1.
FIG. 2B shows a side view of the test strip depicting a mesh and membrane bonded to this test strip.

Referring to FIG. 2A, there is shown a perspective view of a test strip 15, according to this invention. As seen, the test strip 15 has a locating or centering notch 17 located at the top end with aperture 20 showing. Aperture 20 co-acts with the mesh 21A located above the strip 15 and with a membrane 21B located beneath the aperture.

Referring to FIG. 2B, there is shown a side view of the strip 15 with the mesh 21A and the membrane 21B shown. Typically, the test strip has a length of 45.2 mm, with the mesh and the membrane being approximately 9.53 mm in length. The aperture 20 has a diameter between 4 to 5 millimeters and is centered between the mesh and the membrane. The membrane is secured to the back of the test strip overlying the aperture 20 by means of an adhesive, as, for example, one supplied by the 3-M Company designated as No. 9442. The outer or bottom surface 21C of the membrane is a reflective surface. The mesh and the membrane basically are filled and dried with a reagent prior to applying the blood and this reagent is provided at the factory. Each strip, as indicated, has the mesh 21A secured to the top of the strip and has the membrane 21B secured to the back of the strip, both overly the test strip aperture 20. Each strip has a mesh, aperture and membrane that is impregnated with 13 microliters of reagent. One reagent is an aqueous-based solution composed of the following:

1. 1.5% Aerosol TO (sodium dioctyl sulfosuccinate). This is a surfactant which is used to allow the blood to rapidly spread through the membrane.
2. 2.5% Saponin. This is a substance which is derived from Quillaja Bark. This substance is a hemolyzer which is used to lyse erythrocytes, the red blood cells and release the hemoglobin. As one can ascertain, erythrocytes are red blood cells which contain hemoglobin.
3. 2.5% M-700 Maltodextrin. This is a sugar-like material used as a blood diluent, which allows for better sensitivity between samples of similar hemoglobin concentrations.
4. 4.5% Ethanol (200 proof). Ethanol is an alcohol which is used as a co-solvent with water to help to dissolve the components and form a homogenous solution.
5. 0.02% Tartrazine (Acid Yellow 23). This is a yellow dye added as a quality control of measure to make it possible to ascertain which strips have been impregnated with solution. It gives a yellow coloring to the reagent to determine that a particular strip has been impregnated. This yellow dye was chosen, as it is invisible to the LED at 522 nm frequency.

6. 0.005% Phenol (liquefied). This is a preservative used to prevent microbial growth. The remainder is pure deionized water.

Another reagent is an aqueous-based solution composed of the following:
1. 2.5% Benzalkonium Chloride. This is an antimicrobial surfactant which is used to increase wettability allowing the hemolized blood to spread rapidly onto and through the membrane.
2. 2.5% Saponin. This is a substance which is derived from Quillaja Bark. This substance is a hemolyzer which is used to lyse erythrocytes, the red blood cells and release the hemoglobin. As one can ascertain, erythrocytes are red blood cells which contain hemoglobin.
3. 0.02% Tartrazine (Acid Yellow 23). This is a yellow dye added as a quality control measure to make it possible to ascertain which strips have been impregnated with solution. It gives a yellow coloring to the reagent to determine that a particular strip has been impregnated. This yellow dye was chosen, as it is invisible to the LED at 522 nm frequency. The remainder is water.

The reagent is placed in liquid form on the membrane and is then air-dried to evaporate the water and solvents thereby leaving the reagent constituents.

In any event, as one can ascertain, the above percentages are by way of example only, as are the above components. As one will ascertain, there are many co-solvents and dyes and other formulations. It is understood that one is not to be limited in any manner to the components as indicated above and that they are various equivalent substances which will serve as surfactants, hemolyzers, dyes, solvents and so on. The above reagents are preferred reagents and have been successfully utilized together with this particular system.

The test strip 15 is relatively thin, being about 0.01 inches thick. As one can see, the centering notch 17 assures that the test strip 15 is fixed and aligned with respect to the internal hollow of the instrument so that it can have a test performed on it. The instrument 10 contains a unique optical system, suggested in FIGS. 3A and 3D. Located inside the instrument are a pair of LEDs for emitting light at a certain wavelength such as 522 nm. These LEDs are focused in an off-set pattern. At the end of the test sequence, the signal from both LEDs are compared alternatively to determine of the sample volume is adequate and that membrane infiltration and coloration is complete and uniform. The LEDs illuminate the membrane bottom surface and are reflected to a photo detector. The photo detector is positioned to collect a portion of the umbrella of reflected light. In operation, the unit first determines the baseline reflected light signal from the dry, uncolored matrix surface. After the blood is inserted, the test surface is monitored and the reflected light signal from the colored wetted surface of the matrix is recorded. The measured signal indicates the redness of the colored surface and thus, the hemoglobin content of the sample is determined. Actually, the meter measures the percent of remission or reduction in reflected light at 522 nm and converts the percentage remission to percentage hemoglobin using an algorithm contained within the analysis program as will be explained.

The test strip introduction port, slot or aperture 22 and surface 16 are removable for cleaning or is disposable to prevent contamination from user to user. The device can test a small blood sample, which is as little as 10 microliters. The instrument contains a coding system that assures each allotted test strip will provide an accurate result irrespective of lot-to-lot differences in strips due to strip/reagent variations. This coding involves the development, a response curve for each lot of test strip for comparison to the standard curve, which is embedded into the instrument software. A three digit code is then determined for each lot and provided after each test strip lot. This three digit code modifies the resulting reflectance reading in order to best match the standard curve. This helps improve accuracy for manufactured lot to lot.

Figure 3:
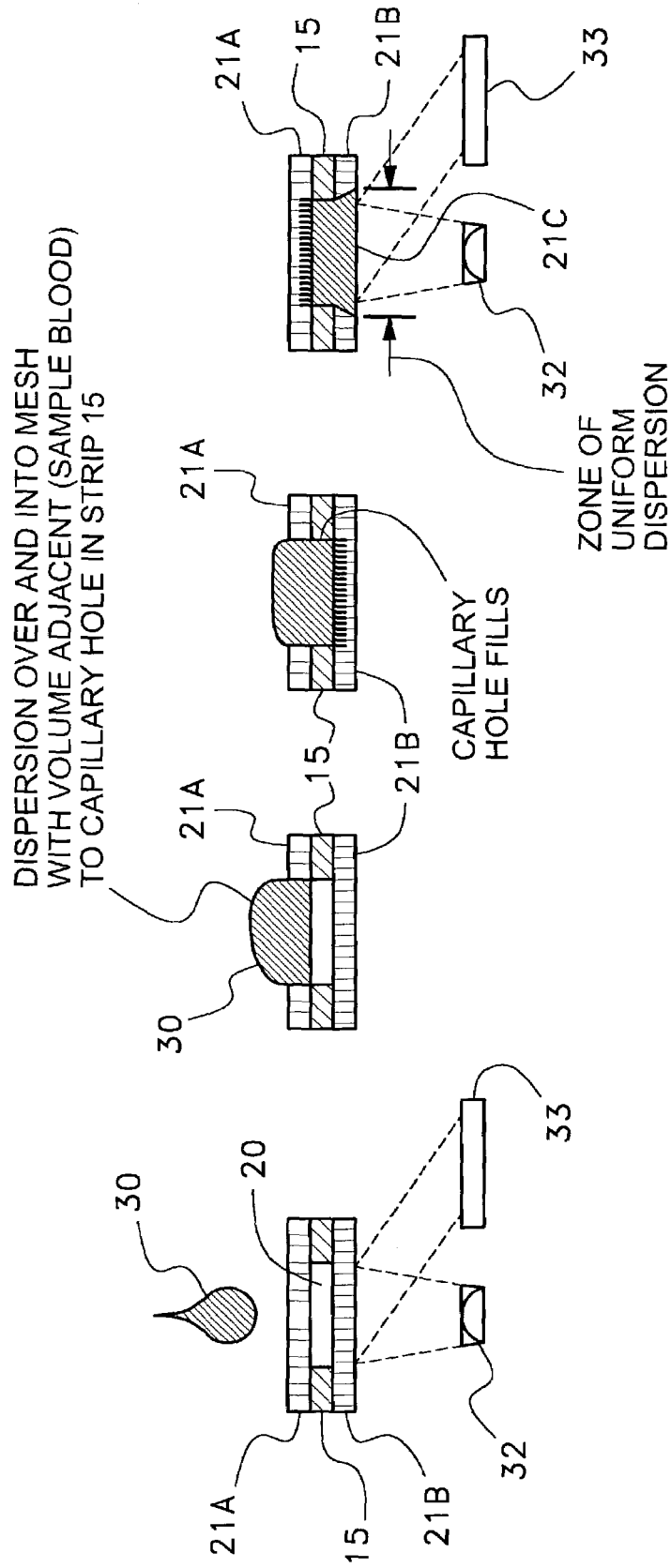
FIG. 3 consists of FIG. 3A to FIG. 3D and depicts four sample sequences in the hemoglobin test strip according to this invention.

Referring now to FIG. 3, there is depicted in FIGS. 3A to 3D the steps performed in utilizing the mesh, the test strip and the membrane according to this invention. The membrane is a nylon matrix of a given porosity and thickness, as will be explained. The test sequence is as follows: The instrument is turned on and the test strip 15 is inserted into the entrance slot or aperture 22 and aligned by notch 17. As seen in FIG. 3A, a drop of blood 30 is then applied to the mesh 21A covered aperture 20. The aperture 20 is clearly visible and highlighted beneath the dispersion mesh 21A. This visibility is enhanced by the color band beneath the mesh interrupted by the aperture 20. The drop of blood 30 disperses or spreads rapidly first into the mesh 21A. Further dispersion occurs as the blood flows through the mesh initially and secondarily into the capillary space created by the aperture 20 and the mesh 21A above and the membrane 21B below. Uniform infiltration into and through the membrane 21B is required to provide the uniform coloration of the membrane 21B test surface and is assured by the dispersion or spreading characteristics of the reagent laden mesh, capillary aperture and finally the membrane itself.

The system includes a kinetic "low volume" or "non-uniform dispersion" test to the red test surface of the membrane 21B before a valid result is posted. The Hgb Meter has a "low-volume threshold" (LVT) designed to give error messages when blood samples of insufficient volume and/or poor placement (e.g. far off-centered) are put in the test strip well. The LVT is based on changes in the remission (i.e. reflectance) measurements of the meter's two 522 nm LEDs. A direct comparison of the remissions of the meter's two LEDs cannot be used, since such a methodology is patented U.S. Pat. No. 6,055,060, which issued on Apr. 25, 2000 and is assigned to Boehringer Mannheim GmbH.

Instead, the LVT uses a kinetic slope analysis technique, where the first LED that drops below 84% remission (% R) (or if both did at the same time, then the one with the lower % R), would be considered the "tracking LED". Once the tracking LED gives similar results (0.1 or less remission units apart) for three consecutive readings (each one second apart), the last two readings of the other LED would be evaluated.

If the last two readings of the non-tracking LED are equal to or less than a certain LVT (set at 0.3 remission units), then it means that both LEDs stabilized around the same time. If both LEDs stabilized around the same time, then it is assumed that both LEDs "saw" similar conditions, and thus there was not a low volume condition (i.e. the test membrane infiltration and coloration was generally uniform). In this case, the calculated percent hemoglobin (Hgb) result would be reported. If the non-tracking LED's last two readings were greater than the 0.3% R LVT, then sample instability and non-uniformity were assumed, and an E-2 error would be displayed.

As the sample infiltrates the porous membrane 21B the LVT algorithm/sequence is initiated by the software, the Hgb-Pro LVT utilizes a color development remission slope analysis. One LED (of the two) tracks the percent remission or absorption. Both LEDs alternatively illuminate and measure. The tracking LED is the first to reach and measure 84% remission. The tracking LED continues to monitor the blood sample as it infiltrates and colors or "reddens" the membrane 21B and the test surface 21C. As the color unifies in the test zone, the color change curve flattens and the remission values get closer and closer. Once the tracking LED gives remission readings within 0.1 difference for three consecutive readings (change in remission vs. change in time). A slope has been created by the system software for the last two readings. For LED #1, the software algorithm then switches on LED #2, takes concurrent readings for the last two and notes the slope of LED #2. If LED #2 meets the LVT of 0.3 remission units (read 2 and read 3 vs. time), then the system concludes that both LEDs "saw" similar conditions and thus, there was not a low volume, (excess slope variation) or non-uniform coloration of the two overlapping test zones. The system will then report the calculated percent of hemoglobin content of the blood sample. If the final two readings of the second LED were greater than the 0.1% to 0.3% remission LVT, then sample instability and non-uniformity, i.e. low volume, an error would be displayed. The system first measures the baseline of the matrix with no blood sample present. An LED 32 illuminates the reflective surface 21C of the matrix. Light is reflected to a photo detector 33, which produces a signal indicative of the baseline value of the matrix surface. This is the reflection from the matrix surface with no blood sample present. The blood sample 30 as seen in FIG. 3A is then applied into the targeted aperture 20 to impregnate and permeate the mesh 21A and the membrane 21B after the test strip is inserted into the instrument. As shown in FIG. 3B, the red cells of the blood sample are now lysed and dispersed into the mesh due to the reagent. As shown in FIG. 3C, the sample continues through the capillary aperture and begins to saturate the membrane, where the sample becomes more fully dispersed. As shown in FIG. 3D dispersion and uniform infiltration is complete and the test surface 21C is fully and uniformly colored by the sample hemoglobin. In FIG. 3D, the LED 32 is again illuminated and the optical measurement area of the surface of the membrane is made with the saturated blood. The unit may repeat the reflectance measurement until two successive readings whose results are within a small programmable difference such as between 0.1 to 0.3% remission are determined. The remission rate of change is monitored in a kinetic way as the hemoglobin wets, fills and reddens the membrane. The LEDs perform a measurement each second and monitor the coloration of the membrane. The flattening of the red coloration response in the photodetector indicates a reaction near completion. This provides a stable output. The percent of remission is determined after comparing the stabilized reading to the baseline reading, as obtained in FIG. 3A. The software converts the percentage remission to a percentage of hemoglobin and that is displayed on the display 18. The conversion is adjusted by the code entry according to strip lot variations.

Again referring to FIG. 3 and to reiterate, the principle of the method discussed is a light reflectance measurement of a hemoglobin sample which permeates a membrane. This is inversely proportional to hemoglobin concentration. As soon as the blood sample contacts the reagent on the membrane, the red blood cells are lysed and the hemoglobin molecules are dispersed on the membrane by the action of the surfactant. This is shown, for example, in FIGS. 3C and 3D.

The hemoglobin meter emits light via the LEDs 32 at 522 nm to the membrane and the intensity of the reflected light is measured by a detector 33. The intensity of the reflected light is converted to hemoglobin concentration by preinstalled software. A copy of the program is appended hereto as Appendix A. Appendix A shows the programming of an Electronically Erasable Programmable Read Only Memory (EEPROM) content for the meter. Going left to right, Appendix A lists the memory's byte location, byte valve (in hex), true values and notes explaining that bytes' functions. This should enable anyone skilled in the art to reproduce the program and to place the contents in an EEPROM or other memory.

The nylon mesh is sold under the trademark "NITEX" and has a pore size of 50–150 micrometers and a thickness of 0.081 millimeters. Such material is supplied by a corporation by the name of SEFAR AMERICA, Inc. The mesh is attached to the strip 15 of FIG. 2A by means of a suitable adhesive. The mesh is translucent, and as such, the printed accent stripe adjacent to the aperture 20 to highlight and accentuate the aperture 20 to facilitate sample application, is acutely visible.

The nylon membrane is sold under the trademark NOVYLON and has a 0.6 to 0.8 µm pore size and a thickness of 0.17 millimeters. Such material is supplied by a corporation by the name of Cuno, Inc. The membrane is attached to the plastic supporting strip 15 of FIG. 2A by means of a suitable adhesive. The supporting strip, as indicated, has the aperture 20, which is 5 millimeters in diameter. The membrane is saturated with a 10 to 15 microliter aliquot of hemoglobin test reagent, which is presented as the sample would be onto the mesh above the center of the hole. The mesh overlay below the membrane are impregnated with the reagent. The impregnated reagent is air-dried or otherwise dried at 50 to 70° C. for 5 to 10 minutes. Alternatively, the reagent can be dried at room temperature for 1 to 2 hours.

As indicated above, the preferred embodiment of the reagent has been indicated, but two reagents have been considered. Each composition contains saponin as a hemolyzing agent and a surfactant. The one reagent contains BAC. The other reagent contains dioctyl sulfosuccinate sodium salt (AOT) with preservatives. The BAC reagent is the preferred reagent. These two reagents perform relatively similarly.

Referring to FIG. 4, there is shown a table which shows a study based on a percent of remission and a percent of hemoglobin utilizing BAC lot reagent which is composed of 2.5% BAC, 2.5% saponin and a small amount of tartrazine. AOT reagent is composed of 1.5% aerosol OT, 2.5% saponin, 2.5% maltodextrin and a small amount of phenol and tartrazine. The table of FIG. 4 is included to indicate that there are other reagents which will suffice and the examples of two reagents, as well as percent remission and percent hemoglobin, are shown in FIG. 4 designated as Table 1.

As one can ascertain, the important parameters involved in hemoglobin measurement by light reflection are the selection of the proper membrane, the dispersion rate of the hemolysate, reagent composition, reagent volume loaded on the membrane strip, and proper volume of the blood sample to be loaded and dispersion through the proper mesh and membrane. All of these parameters have been studied and proper selections have been made. The nylon (NOVYLON) membrane with 0.6 to 0.8 µm pore size has been selected. The reagent volumes could be varied between 10 to 15 microliters per membrane without affecting the measurement results. The blood sample volume could be varied from 10 to 60 microliters for precise measurement of hemoglobin by the above described techniques. The hemoglobin measurement system was tested for its precision and accuracy at the hemoglobin concentration range of 4 to 24%. See FIG. 5.

Shown as FIG. 5, designated as Table II, the present invention hemoglobin measurement is compared to 3 different prior art systems. The manufacturers or method, for example, are shown in the left-hand column. The first being ITC, the applicant herein, or International Technidyne Corporation. The second, Coulter, the third, Hemocue and the fourth, the traditional method, Drabkin. The ITC system operated with 2.5% saponin. For developing Table II, normal blood samples with 16% hematocrit are used. The plasma content was varied by adjusting the plasma volume to prepare low and high hemoglobin concentration samples. First, the hemoglobin content of these blood samples was determined by a reference method. The technique uses a Coulter Counter or Spectrophotometer. This technique is known as cyanmethemoglobinonetry, or the Drabkin Method. This is a fairly accurate technique which produces a spectrum which is indicative of the hemoglobin concentration. The blood samples were tested in the inventive system using the inventive hemoglobin meter with a high intensity light setting (LED intensity of 40 MCD minimum at 522 nm wavelengths) and in the other systems using the appropriate methods.

Figures 6, 6A, 6B, 6C:
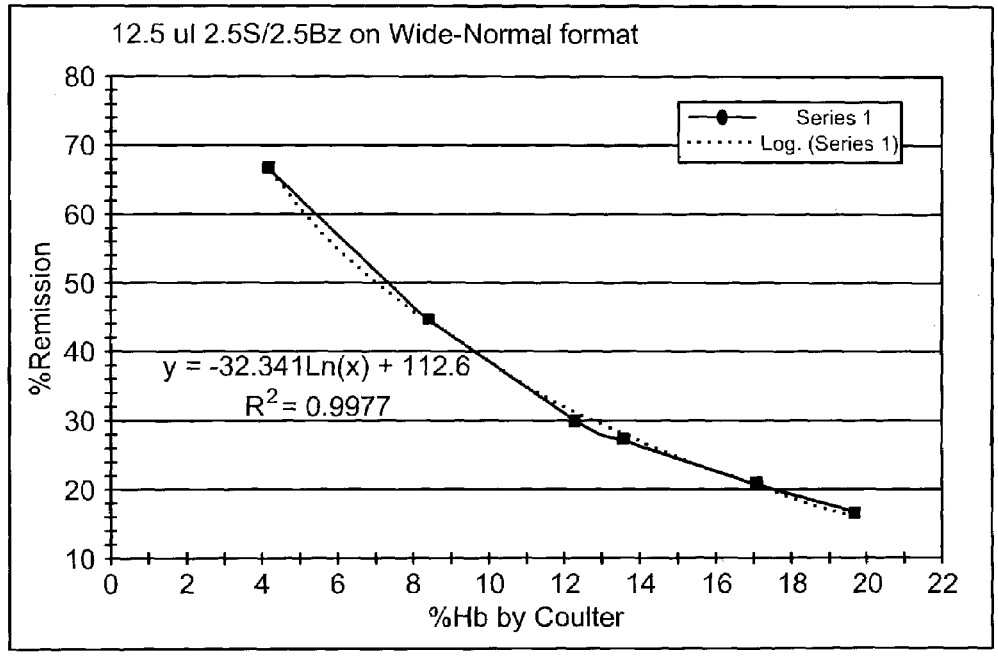
FIG. 6 is a correlation grouping for the BAC reagent and the meter according to this invention.
FIG. 6B compares the Hgb values according to this invention, entered as unconverted Remission values, as compared to a prior art spectrometer device, entered as Hgb.
FIGS. 6A and 6C are the data points used to chart the curve.

Referring to FIG. 6, results are shown utilizing the techniques according to this invention. The Table of FIG. 6A shows the remission of various trials using 2.5% saponin and 2.5% BAC. The center table (6B) compares the percentage of hemoglobin, which is measured by the Coulter Counter, while the bottom FIG. 6C again shows the various trials and percent hemoglobin.

Figures 7, 7A, 7B, 7C:
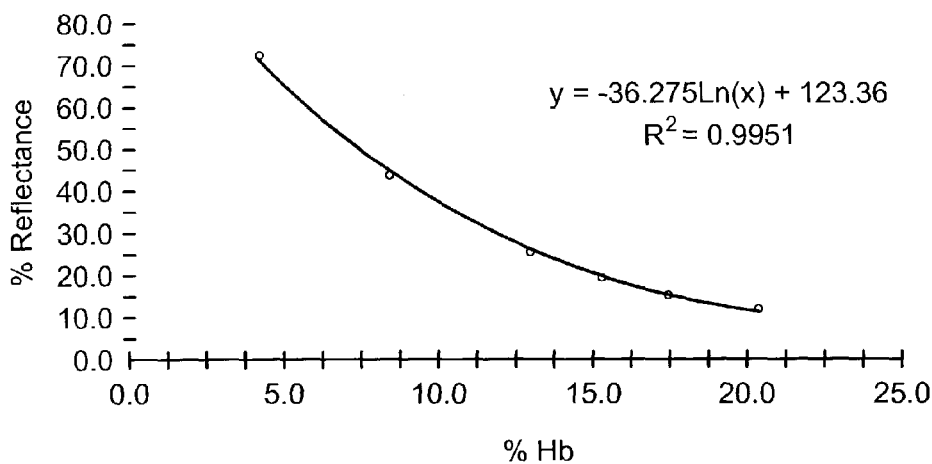
FIG. 7 shows similar correlation tables utilizing the AOT reagent and the meter according to this invention.

FIG. 7 shows the trials using the saponin-AOT mixture utilized with the present invention including the center FIG. 7B, which shows the percentage of hemoglobin measured by this system and showing the table at the bottom (7C). As one can ascertain, the results are relatively identical to those obtained in FIG. 6. The precision of the system, as depicted, for example in FIG. 6C, is good, and the percent of CV is 2.1 or less. The accuracy of the measurement is extremely consistent for hemoglobin concentration range of 4 to 24 g/dl. The blood samples that have been tested were normal male and female, anemic male and female, lymphoma and polycythema samples. See Table III, which is depicted in FIG. 8. This shows the results of the system with female hemoglobin of 12.5 g/dl male hemoglobin 17.35 g/dl, etc. The tables show similar results for the ITC method versus the hemocue reference method.

Blood samples can be utilized from newborn babies, umbilical cord blood, icteric, sickle cell homozygotes, sickle cell heterozygotes, thalassemia, reticulocytosis, and Coumadin treated blood. As one can ascertain, Coumadin is an anti-clotting factor and patients who are taking Coumadin take the drug to prevent clotting. The above described reagent strip is stable at least four weeks at 45 to 60° C. This stability data translates into at least two years of stability at room temperature.

Essentially, as one can ascertain, the system operates to measure the reflection of LED light at a predetermined frequency (522 nm) from the surface of a membrane which is impregnated and colored with blood. One can ascertain that the look up table development protocol can be simply implemented. For example, blood samples for many different levels of hemoglobin concentration can be analyzed multiple times. The analysis of these blood samples regarding data can be stored in memory. Based on the reflection that these samples give from multiple test strips, the reflection data is directly indicative of hemoglobin content. For example, one can take a blood sample having a hemoglobin content of 10 g/dl, impregnate this blood sample in ten membranes and then measure the reflectivity of all ten membranes and take a mean value. Therefore, when the reflectance (remission) is the same during a test, one searches for the stored value and then determines that there is a hemoglobin content of 10 g/dl. In any event, the process is repeated with multiple donors to build data points and equations. Necessary factors for conversion of reflectance data to hemoglobin are easily developed and one can prepare a look-up table. The table is stored in a memory and installed therein to make a determination of the hemoglobin readings from measured reflectance.

Therefore, as one can ascertain, in accordance with the technique depicted in FIG. 3, once the detector determines a particular amount of reflectance, this amount of reflectance is then compared with a look-up table stored in memory. The memory is searched through to find the closest match in detector values to provide a hemoglobin value. In this manner, the hemoglobin content would be consistent with the hemoglobin content listed in the look-up table as equivalent to a given percentage of reflection measurement. The LED 32 in FIG. 3 can be pulsed on and off, and each time it is pulsed on and off a measurement is made. When two consecutive measurements are within 0.1 to 0.3%, then one will ascertain kinetically that this is the optimum reflection result. The system then takes the reflectance measurement, after the low volume check is completed and determined to be satisfactory, and compares it with all data stored in memory. The system then makes and takes the remission and derives a concentration (g/dl or mmol/L) of hemoglobin for that data. As shown in Appendix A, memory as (ROM, RAM, EEPROM) and so on is loaded with known hemoglobin values indicative of reflection signals. The comparison or search is easily implemented by any microprocessor or by suitable circuitry. The technique of receiving an unknown signal value in this case from the detectors and then reading the content of the memory for the closest comparison includes interpolative techniques and is not considered separately distinct from this invention.

It is therefore seen that the test is an extremely accurate and rapid method of determining hemoglobin content from a blood sample which can be performed by a relatively unskilled person. It should be apparent to those skilled in the art that there are many alternatives available and many equivalents available, as should be discerned by those skilled in the art. For example, there may be different reagents which will perform as the reagent described above, as well as different types of meshes and membranes, as well as different test procedures all using the reflectance of light to provide a meter reading. All of these will be considered to be encompassed within the spirit and scope of this invention as defined by the appended claims.

The hemoglobin system described herein utilizes a reagent/strip compensation technique. This adjustment to the look up table is based on a code number entry into the meter. The code can adjust the look up table up or down, left or right, creating a new curve based on data from tests to determine the reagent/strip characteristics. Using a complex algorithm, a calibration system compares test results of a given lot of strips, tested by a known reference method, using a series of controls to a baseline curve and adjusts accordingly. Thus, a given blood sample should give virtually the same values, irrespective of strip lots.

What is claimed is:

1. An apparatus for quickly measuring the hemoglobin content of a blood sample, the apparatus comprising:
   a test strip;
   a mesh supported by said test strip, said mesh impregnated with a lysing reagent, wherein said blood sample applied to said mesh disperses across said mesh and reacts with said lysing reagent impregnated in said mesh;
   a porous substrate supported by said test strip, said porous substrate impregnated with said lysing reagent and having a light reflecting surface;
   a light source selectively operated to illuminate said reflecting surface of said substrate to cause a predetermined amount of light to reflect from said substrate according to the hemoglobin content of said blood sample;

a detector for intercepting said reflected light to provide a signal indicative of the magnitude of said reflected light;

an indicator responsive to said signal for providing an output indicative of said hemoglobin content.

2. The apparatus according to claim 1 wherein said porous substrate comprises a nylon material with a pore size between 0.6 to 0.8 μm.

3. The apparatus according to claim 1 wherein said reagent includes a hemolyzing agent and a surfactant.

4. The apparatus according to claim 3 wherein said hemolyzing agent is saponin.

5. The apparatus according to claim 4 wherein said surfactant is sodium dioctyl sulfosuccinate (AOT), or Benzalkonium Chloride (BAC).

6. The apparatus according to claim 5 wherein said reagent includes at least 1% of surfactant, at least 2% of saponin, maltodextrin, ethanol and some dye colorant and some preservative with the remainder being water or BAC.

7. The apparatus according to claim 1 wherein said light source is at a wavelength of between 500 to 550 nm.

8. The apparatus according to claim 1 wherein said sample of blood is between 10 to 60 microliters.

9. The apparatus according to claim 1 wherein said reagent is 10 to 15 microliters per substrate.

10. The apparatus according to claim 1 wherein said hemoglobin content of said blood sample can vary between 4 to 24 g/dl of said blood sample volume.

11. Apparatus for measuring the hemoglobin content of a blood sample, the apparatus comprising:
a housing having an internal hollow with a front opening accessing said hollow;
a test strip having an aperture on a surface thereof, said test strip adapted to be inserted into said housing front opening a given distance to cause said test aperture strip to be positioned over said housing and accessible with said hollow, said strip having a mesh covering a sample application side of the aperture and a porous membrane covering a bottom of said aperture, said membrane having a light reflecting surface facing said hollow when said strip is inserted, said mesh and membrane impregnated with a lysing reagent, wherein a blood sample applied to said mesh disperses across said mesh and reacts with said lysing reagent impregnated in said mesh;
a light source located in said housing hollow and positioned to illuminate said light reflecting surface of said membrane;
a detector located in said housing hollow for receiving reflected light from said membrane and for providing a signal indicative of the intensity of said reflected light; and
a comparator for comparing said signal with stored signals to produce an output indicative of hemoglobin content as determined by light reflected from said membrane surface.

12. The apparatus according to claim 11 wherein said membrane comprises a nylon material with a pore size of between 0.6 to 0.8 μm and between 0.16 to 0.18 millimeters thick.

13. The apparatus according to claim 11 where said reagent contains a hemolyzing agent and a surfactant.

14. The apparatus according to claim 13 wherein said hemolyzing agent is saponin and said surfactant is BAC or AOT.

15. A method of determining the amount of hemoglobin in a blood sample, the method comprising the steps of:
lysing a sample of blood with a test strip comprising a mesh and a membrane having a reflective surface, said mesh and membrane impregnated with a lysing reagent, said lysing performed by applying said blood sample to said mesh, wherein said blood sample applied to said mesh disperses across said mesh and reacts with said lysing reagent impregnated in said mesh;
directing a beam of light on said reflective surface to cause an amount of light to be reflected according to the blood lysed;
intercepting said reflected beam to provide a signal indicative of the amount of said reflected light;
comparing said signal with stored calibration signals indicative of tested reflected light from known blood samples;
providing a value indicative of the hemoglobin content of said sample interpolating between closest compared values.

16. The method corresponding to claim 15, comprising the steps of first providing a reflected light signal from said membrane before lysing said sample of blood.

17. The method according to claim 15 wherein said light has a wavelength of 522 nm.

18. The method according to claim 15 wherein said membrane is nylon having a pore size of about 0.6 to 0.8 μm with a thickness of about 0.15 millimeters, to accommodated 10 to 15 microliter aliquot of reagent.

19. The method according to claim 18 wherein said reagent contains a saponin hemolyzing agent and a BAC or AOT reagent.

20. The method according to claim 15 wherein said reagent contains 2.5% saponin, 2.5% maltodextrin, 1.5% AOT, 0.002% coloring, a small amount of phenol and tartrazine and the remainder being water, or, 2.5% saponin, 2.5% BAC, 0.002% coloring and the remainder water.

21. The method according to claim 15, wherein the amount of hemoglobin in the blood sample is determined in 5 to 29 seconds.

22. A method of determining the amount of hemoglobin in a blood sample, the method comprising the steps of:
lysing a sample of blood into a membrane having a reflective surface and containing a reagent suitable for lysing said sample;
directing a beam of light on said reflective surface to cause an amount of light to be reflected according to the blood lysed;
intercepting said reflected beam to provide a signal indicative of the amount of said reflected light;
comparing said signal with stored calibration signals indicative of tested reflected light from known blood samples;
providing a value indicative of the hemoglobin content of said sample interpolating between closest compared values;
performing a kinetic measurement including the steps of taking reflectance reading every 1 second and declaring an end point when the difference in two consecutive readings is under a predetermined percentage.

23. The method according to claim 22, further including determining uniformity and adequacy of a sample coloration of the reflective surface utilizing a Kinetic Low Volume Threshold technique which compares a slope created by end point readings for two consecutive readings of Remission values of a test LED to a slope created by two comparable readings of a second LED as criteria that test completion has been reached.

24. A method of determining the amount of hemoglobin in a blood sample, comprising the steps of:
  lysing a sample of blood with a test strip comprising a mesh and a membrane having a reflective surface, said mesh and membrane impregnated with a lysing reagent, said lysing performed by applying said blood sample to said mesh, wherein said blood sample applied to said mesh disperses across said mesh and reacts with said lysing reagent impregnated in said mesh;
  directing a beam of light on said reflective surface to cause a reduction in the amount of light to be reflected according to the blood lysed, the hemoglobin released and the light absorption of that hemoglobin;
  intercepting said reflected beam to provide a signal indicative of the amount of said reflected light;
  comparing said signal with stored calibration signals indicative of tested reflected light from known blood samples, and a blank test surface without sample;
  providing a value indicative of the hemoglobin content of said sample according to said closest compared stored signal, adjusted to each strip lot by the code member.

25. A test strip for use with an apparatus that measures a hemoglobin content of a blood sample, the test strip comprising:
  a supporting strip;
  a mesh disposed on the supporting strip, the mesh impregnated with a lysing reagent; and
  a membrane disposed on the supporting strip adjacent to the mesh, the membrane impregnated with the lysing reagent and having a light reflecting surface,
  wherein the blood sample applied to the mesh disperses across the mesh and reacts with the lysing reagent impregnated in the mesh.

26. The test strip according to claim 25, wherein the reagent includes sodium dioctyl sulfosuccinate (AOT), or Benzalkonium Chloride (BAC).

* * * * *